(12) United States Patent
Goyal et al.

(10) Patent No.: US 10,444,219 B2
(45) Date of Patent: Oct. 15, 2019

(54) PREDICTIVE MODELING TO ESTIMATE DATA VALUES BETWEEN SAMPLING EVENTS

(71) Applicant: International Business Machines Corporation, Armonk, NY (US)

(72) Inventors: Aanchal Goyal, White Plains, NY (US); Younghun Kim, White Plains, NY (US); Tarun Kumar, Mohegan Lake, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 262 days.

(21) Appl. No.: 15/076,042

(22) Filed: Mar. 21, 2016

(65) Prior Publication Data
US 2017/0269055 A1 Sep. 21, 2017

(51) Int. Cl.
*G01N 33/28* (2006.01)
*G01N 33/00* (2006.01)

(52) U.S. Cl.
CPC . *G01N 33/2841* (2013.01); *G01N 2033/0068* (2013.01)

(58) Field of Classification Search
CPC ...... G01N 33/2841; G06N 5/02; G06N 7/005; G01R 31/1281; G01R 31/02; G01R 31/14; G01R 31/3271; H01F 27/12; H01F 27/402; H01F 2027/404; H02H 5/08
USPC .......... 706/45, 46, 50; 702/6, 58, 183, 181, 702/182, 184; 324/553
See application file for complete search history.

(56) References Cited

U.S. PATENT DOCUMENTS

| | | | |
|---|---|---|---|
| 7,474,186 B2 | 1/2009 | Altmann | |
| 7,747,417 B2 | 6/2010 | Lamontagne | |
| 8,347,687 B2 | 1/2013 | Cunningham | |
| 2012/0290229 A1* | 11/2012 | Cavallini | G01N 33/2841 702/58 |
| 2013/0204827 A1* | 8/2013 | Kawachi | G01N 33/2841 706/46 |
| 2014/0260529 A1 | 9/2014 | Pruente et al. | |
| 2015/0020572 A1 | 1/2015 | Kim et al. | |

FOREIGN PATENT DOCUMENTS

WO 9836265 A1 8/1998

OTHER PUBLICATIONS

Duval et al., "Improving the Reliability of Transformer Gas-in-Oil Diagnosis" Electrical Insulation Magazine, IEEE vol. 21, No. 4, Jul./Aug. 2007, pp. 21-27.

* cited by examiner

*Primary Examiner* — Mouloucoulaye Inoussa
(74) *Attorney, Agent, or Firm* — Cantor Colburn LLP; Grant Johnson (57) ABSTRACT

Disclosed herein are systems, methods, and computer-readable media for utilizing sensor data captured by one or more sensors as well as ground-truth physically sampled data to generate a predictive model that can be used to estimate a measurable parameter without having to obtain additional physically sampled data for the parameter.

17 Claims, 5 Drawing Sheets

PREDICTIVE MODELING TO ESTIMATE DATA VALUES BETWEEN SAMPLING EVENTS

BACKGROUND

Performing fault diagnostics for equipment typically involves taking direct measurements relating to operating characteristics of the equipment and analyzing the measured data to detect the presence of fault modes. For example, in the case of oil-immersed transformers, conventional fault detection methods involve direct measurement of dissolved gas concentration levels in the oil. Conventional fault detection methods that involve direct measurement of quantities, however, suffer from a number of drawbacks. For example, in the case of oil-immersed transformers, direct measurement of dissolved gas concentration levels is a cumbersome process that requires extracting the oil from the transformer and directly sampling the oil to obtain measurements. Technical solutions that address at least some of these drawbacks are described herein.

SUMMARY

In one or more example embodiments of the disclosure, a method is disclosed that includes obtaining first data relating to a measurable parameter, the first data being obtained by directly measuring the measurable parameter in a physical sample associated with equipment; obtaining second data comprising sensor data captured by one or more sensors, the sensor data relating to one or more operating parameters of the equipment; determining one or more cumulative statistics from the sensor data; generating the predictive model using the one or more cumulative statistics and the first data; and estimating a value of the measurable parameter using the predictive model.

In one or more other example embodiments of the disclosure, a system is disclosed that includes at least one memory storing computer-executable instructions; and at least one processor configured to access at least one memory and execute the computer-executable instructions to: obtain first data relating to a measurable parameter, the first data being obtained by directly measuring the measurable parameter in a physical sample associated with equipment; obtain second data comprising sensor data captured by one or more sensors, the sensor data relating to one or more operating parameters of the equipment; determine one or more cumulative statistics from the sensor data; generate the predictive model using the one or more cumulative statistics and the first data; and estimate a value of the measurable parameter using the predictive model.

In one or more other example embodiments of the disclosure, a computer program product is disclosed that comprises a non-transitory storage medium readable by a processing circuit, the storage medium storing instructions executable by the processing circuit to cause a method to be performed. The method includes obtaining first data relating to a measurable parameter, the first data being obtained by directly measuring the measurable parameter in a physical sample associated with equipment; obtaining second data comprising sensor data captured by one or more sensors, the sensor data relating to one or more operating parameters of the equipment; determining one or more cumulative statistics from the sensor data; generating the predictive model using the one or more cumulative statistics and the first data; and estimating a value of the measurable parameter using the predictive model.

BRIEF DESCRIPTION OF THE DRAWINGS

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. In the drawings, the left-most digit(s) of a reference numeral identifies the drawing in which the reference numeral first appears. The use of the same reference numerals indicates similar, but not necessarily the same or identical components. However, different reference numerals may be used to identify similar components as well. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

DETAILED DESCRIPTION

Overview

Disclosed herein are systems, methods, and computer-readable media for utilizing sensor data captured by one or more sensors as well as ground-truth physically sampled data to generate a predictive model that can be used to estimate a measurable parameter without having to obtain additional physically sampled data for the parameter. In an example embodiment of the disclosure, the sensor data may be supervisory control and data acquisition (SCADA) data obtained by a remote monitoring and control system, while the physically sampled data may be data obtained by direct measurement of a physical sample. Further, in certain example embodiments, the predictive model that is generated may be used to estimate a current concentration of dissolved gas in oil of an oil-immersed transformer without having to obtain a physical sample of the oil and directly measure the concentration levels.

Electric power distribution systems may include transformers such as, for example, step-down transformers that decrease a primary alternating current (AC) voltage from a source (e.g., a transmission line) to a lower secondary AC voltage provided to a destination (e.g., a distribution line); step-up transformers that increase a primary voltage to a higher secondary voltage; or the like. Such transformers may be immersed in oil. The oil may serve as a coolant due to its higher heat capacity than air. The oil may also act as a sealant to prevent air from reaching certain internal components of the transformer, thereby mitigating the likelihood of oxidation and rust formation.

Various operating conditions may cause a transformer to age over time. For example, high loading conditions, high temperature conditions, unstable electrical conditions that may cause arcing or sparking, and so forth may result in diminished performance of a transformer over time. Such conditions that lead to diminished transformer performance over time may result in a phenomenon where concentrations of dissolved gas components in the oil increase over time.

Conventional fault detection techniques for oil-immersed transformers include dissolved gas analysis (DGA) which involves obtaining a sample of the oil and directly measuring the concentration levels of various gas components in the oil. If a fault condition is determined to exist based on the DGA sampled data, a corrective measure may be taken such as, for example, replacing the oil. DGA, however, can be a cumbersome process requiring extraction of the oil from the transformer, direct measurement of the dissolved gas concentration levels in the oil, and replacement of the oil. As such, DGA is typically performed at discrete periodic intervals, and as a result, how dissolved gas concentration levels change between sampling events may not be known when DGA alone is used to determine dissolved gas concentration levels at discrete intervals.

In accordance with example embodiments of the disclosure, sensor data captured from one or more sensors such as, for example, SCADA data may be used in conjunction with historical DGA data to generate a predictive model that can be used to estimate dissolved gas concentration levels in oil of an oil-immersed transformer between DGA sampling events and at any future time. More specifically, the sensor data may be analyzed to determine one or more types of cumulative statistics. The types of statistics determined may include, without limitation, descriptive statistics such as, for example, total cumulative load on the transformer, sample variance, standard deviation, higher order harmonics, or the like of voltage or current distortions; accelerated decomposition condition statistics relating to degradation conditions associated with the transformer over time; and accelerated decomposition event statistics relating to particular events monitored over time. Accelerated decomposition condition statistics may be features calculated based on a specific threshold value of a sensed parameter such as, for example, the sum of the load exceeding X % of the rated capacity of the transformer. Accelerated decomposition event statistics may include, for example, a number of switching cycles of tap changers, a number of times a loading threshold is crossed, or the like. Accelerated decomposition event statistics may effectively capture potentially damaging events for the transformer that may not be captured by a descriptive statistics or an accelerated decomposition condition statistic. Further, accelerated decomposition event statistics may capture both high energy and low energy partial discharge events.

An optimization problem may then be solved whereby a difference between a change in dissolved gas concentration levels between two sampling events (a sampling event at time $t_1$ and a sampling event at time $t_2$) and a function of the cumulative statistics determined based on sensor data accumulated between time $t_1$ and a sampling event at time $t_2$ is minimized. The solution to the optimization problem may be a predictive model that may be used to estimate dissolved gas concentration levels at any time between time $t_1$ and time $t_2$ and/or to predict dissolved gas concentration levels at some future time.

Illustrative Systems, Methods, and Computer-readable Media

Figure 1:
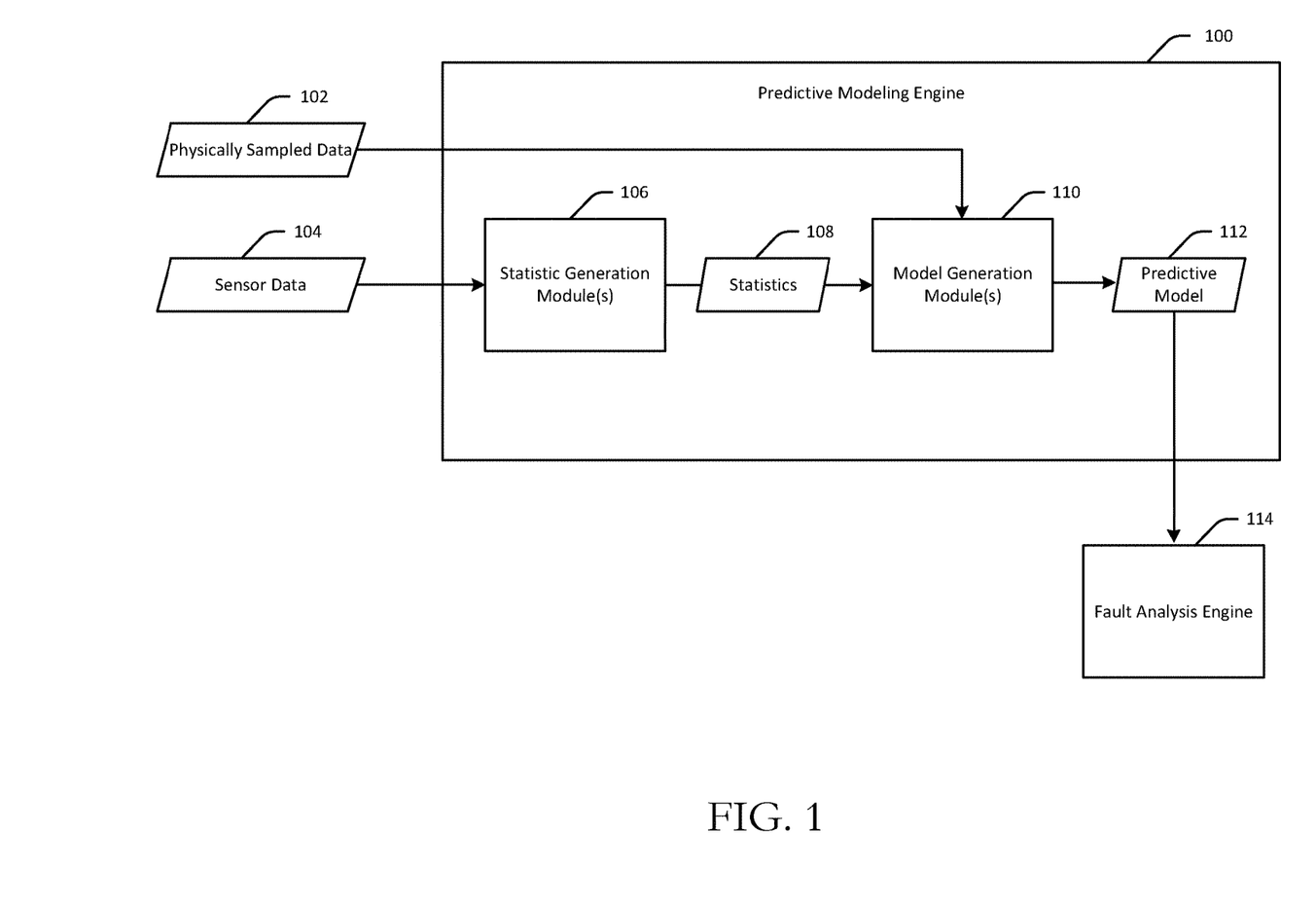
FIG. 1 schematically depicts an illustrative operation of a predictive modeling engine in accordance with one or more example embodiments of the disclosure.
Figure 2:
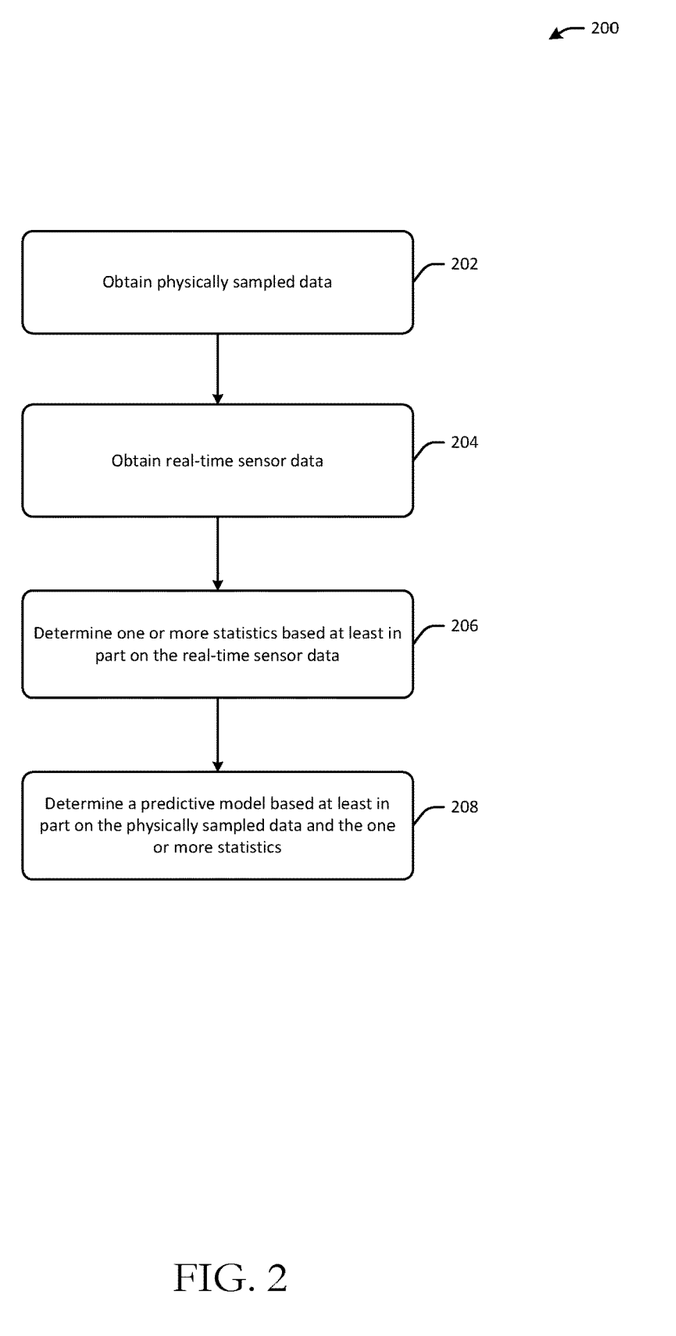
FIG. 2 is a process flow diagram of an illustrative method for determining a predictive model in accordance with one or more example embodiments of the disclosure.

FIG. 1 schematically depicts an illustrative operation of a predictive modeling engine in accordance with one or more example embodiments of the disclosure. FIG. 2 is a process flow diagram of an illustrative method 200 for determining a predictive model in accordance with one or more example embodiments of the disclosure. FIG. 1 will be described hereinafter in conjunction with FIG. 2.

Referring first to FIG. 1, a predictive modeling engine 100 is shown. The predictive modeling engine 100 may be implemented on a computing device containing one or more processing units configured to execute computer-executable instructions, program code, or the like of the predictive modeling engine 100 to cause one or more corresponding operations to be performed. In certain example embodiments, the predictive modeling engine 100 may include one or more program modules such as, for example, one or more statistic generation modules 106 and one or model generation modules 110. Each such module may include computer-executable instructions, code, or the like that responsive to execution by one or more processing circuits may cause more specialized tasks or operations to be performed. It should be appreciated that the predictive modeling engine 100 may include any number of additional modules or sub-modules. Further, at times herein, the terms engine, module, or program module may be used interchangeably.

Referring now to FIGS. 1 and 2 in conjunction with one another, at block 202 of method 200, physically sampled data 102 may be obtained. The physically sampled data 102 may be obtained by direct measurement of one or more parameters such as, for example, direct measurement of dissolved gas concentration levels in a sample of oil associated with an oil-immersed transformer.

At block 204, sensor data 104 captured by one or more sensors may be obtained. The sensor data may be, for example, SCADA data obtaining by a remote monitoring and control system. The SCADA data may include data captured by temperature sensors, voltage load sensors, or the like.

At block 206, computer-executable instructions, program code, or the like of the statistic generation module(s) 106 may be executed to determine one or more statistics 108 based at least in part on the sensor data 104. The statistics 108 may be cumulative statistics including, without limitation, descriptive statistics indicative of the instantaneous values of sensed parameters; accelerated decomposition condition statistics relating to degradation conditions occurring over time; accelerated decomposition event statistics relating to particular events monitored over time; and so forth.

At block 208, computer-executable instructions, program code, or the like of the model generation module(s) 110 may be executed to determine a predictive model 112 based at least in part on the one or more statistics 108 determined by the statistic generation module(s) 106 and the physically sampled data 102. More specifically, the model generation module(s) 110 may be executed to determine a solution to an optimization problem that minimizes a difference between the physically sampled data 102 and an output of a function of the cumulative statistics. In certain example embodiments, the optimization problem may be mathematically modeled as follows: $\mathrm{argmin}_{F,\theta j,\ \varepsilon j} \|\Delta(t_s, t_e) - F(f_{ds,j}, f_{ac,j}(\theta_j), f_{ad,j}(\varepsilon_j))\|$, where $\Delta(t_s, t_e)$ represents the change in a measured parameter between a sampling event at time $t_s$ and a sampling event at time $t_e$; $f_{ds,j}$ represents descriptive statistics; $f_{ac,j}(\theta_j)$ represents accelerated decomposition condition statistics; and $f_{ad,j}(\varepsilon_j)$ represents accelerated decomposition event statistics.

The predictive model 112 may be used to estimate or predict values of parameters to which the physically sampled data 102 relates without necessitating additional gathering of physically sampled data. More specifically, a fault analysis engine 114 may receive the predictive model 112 as input, and may determine whether a fault condition may be present or may occur in the future based on estimated or predicted values of parameters to which the physically sampled data 102 relates.

Figure 3:
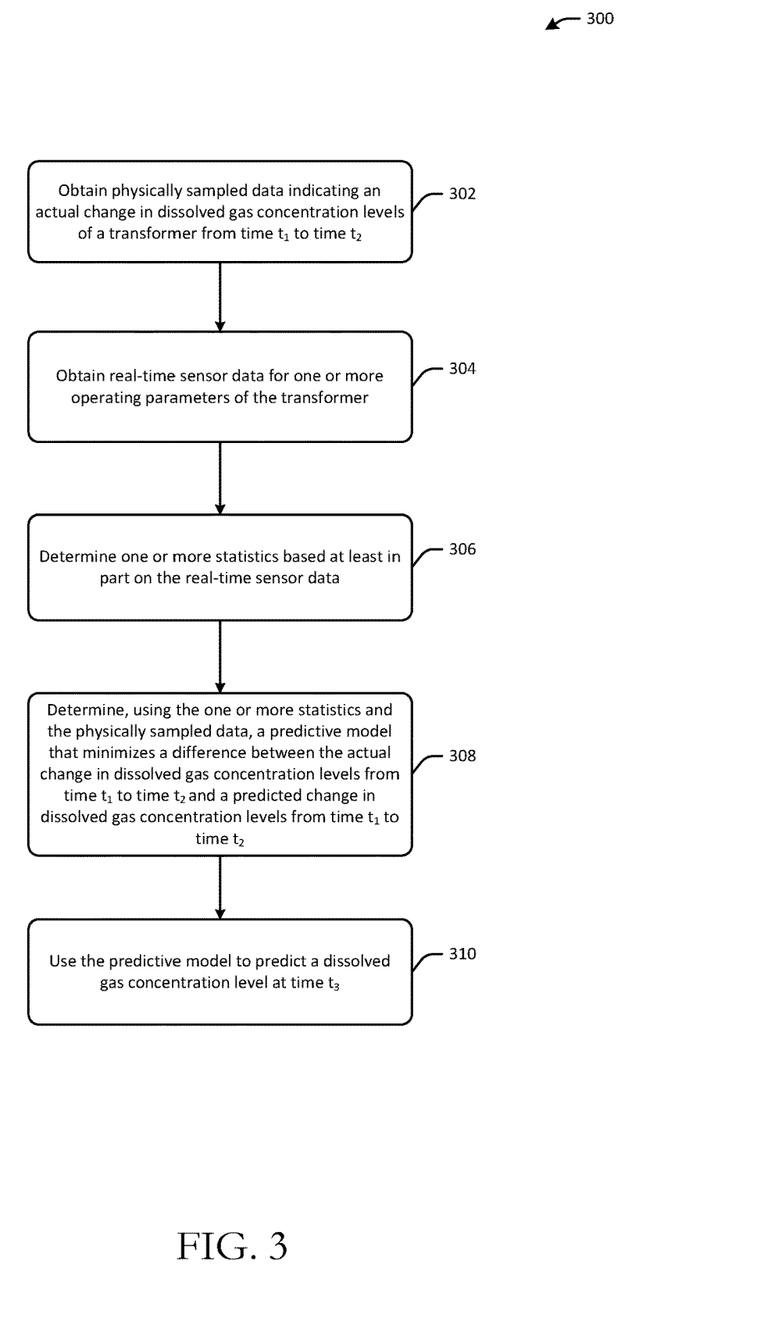
FIG. 3 is a process flow diagram of a more detailed illustrative method for determining a predictive model to estimate dissolved gas concentration levels in an oil-immersed transformer in accordance with one or more example embodiments of the disclosure.

FIG. 3 is a process flow diagram of a more detailed illustrative method for determining a predictive model to estimate dissolved gas concentration levels in an oil-immersed transformer in accordance with one or more example embodiments of the disclosure. FIG. 3 will be described in conjunction with FIG. 1 hereinafter.

Referring now to FIGS. 1 and 3 in conjunction with one another, at block 302 of method 300, the physically sampled data 102 may be obtained. The physically sampled data 102 may include DGA data obtained by directly measuring the concentration levels of various gas components in oil retrieved from an oil-immersed transformer at two discrete points in time—time $t_1$ and time $t_2$. More generally, the physically sampled DGA data 102 may include measured gas concentration levels obtained at discrete periodic intervals, and thus, may indicate gas concentration levels at discrete points in time corresponding to the sampling events, but may not provide any indication of how the gas concentrations levels are varying during time periods between the sampling events. For example, the physically sampled data 102 may provide no indication as to how gas concentration levels may have varied between time $t_1$ and time $t_2$.

At block 304, the sensor data 104 captured by one or more sensors may be obtained. The sensor data may be, for example, SCADA data obtained in real-time by one or more sensors remotely monitoring various operating parameters of the transformer (e.g., voltage load, temperature, etc.).

At block 306, computer-executable instructions, program code, or the like of the statistic generation module(s) 106 may be executed to determine one or more statistics 108 based at least in part on the sensor data 104. The types of statistics 108 determined may include, without limitation, descriptive statistics such as, for example, total cumulative load on the transformer, sample variance, standard deviation, or the like; accelerated decomposition condition statistics relating to degradation conditions associated with the transformer over time; and accelerated decomposition event statistics relating to particular events monitored over time. Accelerated decomposition condition statistics may be features calculated based on a specific threshold value of a sensed parameter such as, for example, the sum of the load exceeding X % of the rated capacity of the transformer. Accelerated decomposition event statistics may include, for example, a number of switching cycles of tap changers, a number of times a loading threshold is crossed, or the like. An accelerated decomposition condition may be an operating condition associated with the transformer that is sustained for a threshold period of time (e.g., the sum of the transformer load exceeding X % of the rated capacity of the transformer for a threshold period of time). An accelerated decomposition event may be a sharp and abrupt change in an operating condition of the transformer (e.g., crossing of a loading threshold).

At block 308, computer-executable instructions, program code, or the like of the model generation module(s) 110 may be executed to determine a predictive model 112 based at least in part on the statistics 108 determined by the statistic generation module(s) 106 and the physically sampled data 102. The predictive model 112 may be one that minimizes a difference between the actual change in dissolved gas concentration levels between time $t_1$ and time $t_2$ and a predicted change in gas concentration levels between time $t_1$ and time $t_2$.

More specifically, the model generation module(s) 110 may be executed to determine a solution to an optimization problem that minimizes a difference between the physically sampled data 102 and an output of a function of the cumulative statistics. The optimization problem may be mathematically modeled as follows: $\mathrm{argmin}_{F,\theta j,\ \varepsilon j} \|\Delta g_i(t_s, t_e) - F(f_{ds,j}, f_{ac,j}(\theta_j), f_{ad,j}(\varepsilon_j))\|$, where $\Delta g_i(t_s, t_e)$ represents the change in a measured concentration level of a ith gas component between the measured concentration level at time $t_s$ and the measured concentration level at time $t_e$; $f_{ds,j}$ represents descriptive statistics relating to operation of the transformer; $f_{ac,j}(\theta_j)$ represents accelerated decomposition condition statistics relating to operation of the transformer; and $f_{ad,j}(\varepsilon_j)$ represents accelerated decomposition event statistics relating to operation of the transformer.

The formulation $F(f_{ds,j}, f_{ac,j}(\theta_j), f_{ad,j}(\varepsilon_j))$ can be represented as a linear $$\text{combination } A \begin{bmatrix} fds, j \\ \mathrm{hull}(fac, j(\theta j)) \\ \mathrm{hull}(fad, j(\varepsilon j)) \end{bmatrix}$$

such that the optimization problem can be represented as $$\mathrm{argmin}_{F,\theta j,\varepsilon j} \left\| \Delta g_i(t_s, t_e) - A \begin{bmatrix} fds, j \\ \mathrm{hull}(fac, j(\theta j)) \\ \mathrm{hull}(fad, j(\varepsilon j)) \end{bmatrix} \right\|.$$

The hull operations may ensure that the optimization problem is convex so that one or more global optima may be determined. Because the hull operations guarantee that the optimization problem is a convex optimization, the optimization problem may be further represented by the affine mapping $$A \begin{bmatrix} fds, j \\ \mathrm{hull}(fac, j(\theta j)) \\ \mathrm{hull}(fad, j(\varepsilon j)) \end{bmatrix} - \Delta g_i(t_s, t_e)$$

that eliminates that normalization (or absolute value) since the affine mapping does not change convexity.

The predictive model 112 may then be used to estimate or predict values of parameters to which the physically sampled data 102 relates without necessitating additional gathering of physically sampled data. More specifically, at block 310, the predictive model 112 may be used to predict a dissolved gas concentration level of a gas component at a time $t_3$ that occurs between times $t_1$ and $t_2$, prior to time $t_1$, or after time $t_2$.

Figure 5:
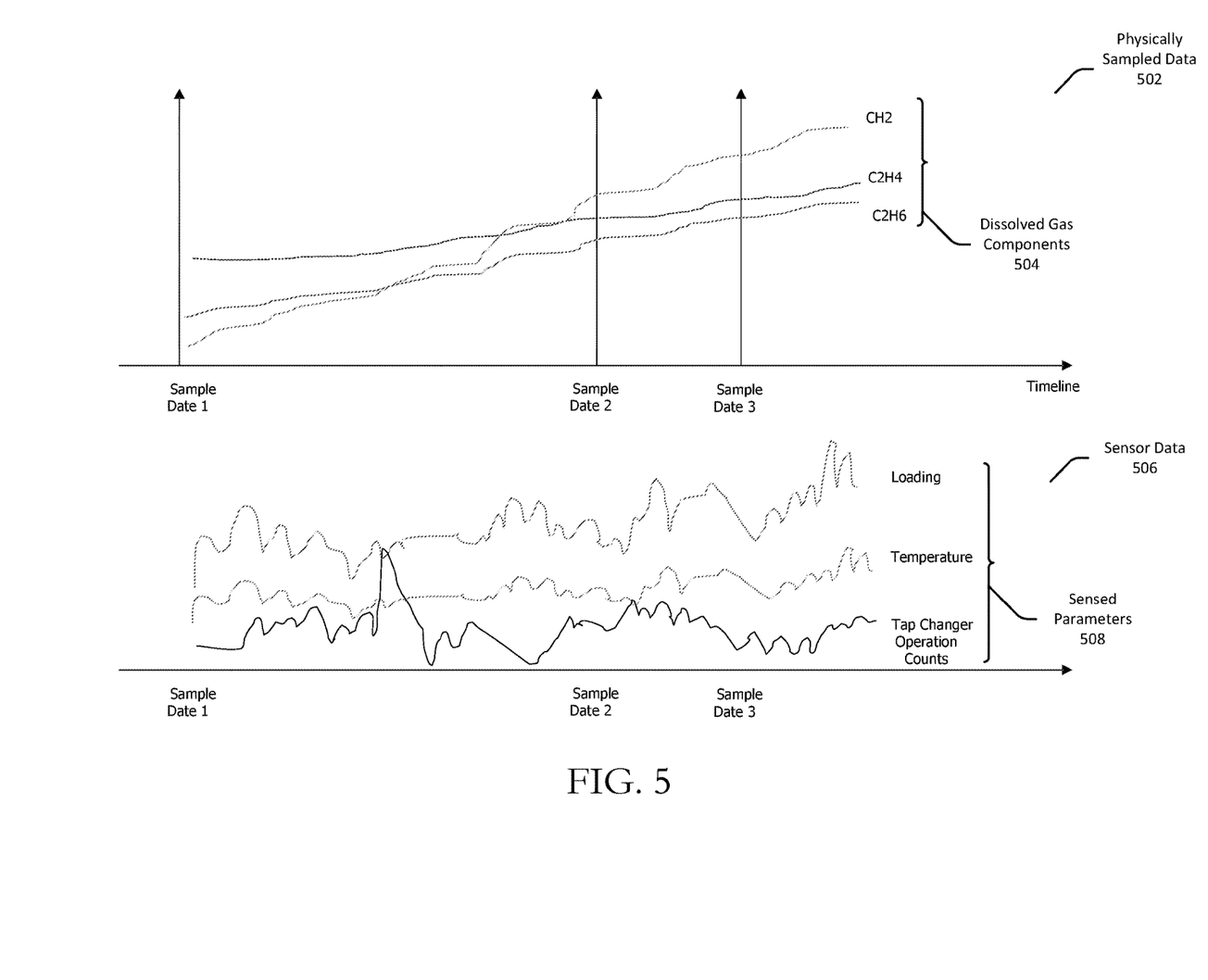
FIG. 5 illustrates a graph of dissolved gas concentration levels as determined using a predictive model generated using physically sampled data and sensor data in accordance with one or more example embodiments of the disclosure.

FIG. 5 illustrates a graph of dissolved gas concentration levels as determined using a predictive model generated using physically sampled data 502 and sensor data 506 in accordance with one or more example embodiments of the disclosure. In particular, the physically sampled data 502 may indicate the measured gas concentration levels of various dissolved gas components 504 at particular sampling dates. The sensor data 506 may include data relating to one or more sensed parameters 508. As previously described, various cumulative statistics may be determined from the sensor data 506, and a predictive model may be determined using the cumulative statistics and the physically sampled data 502. The predictive model may then be used to estimate the gas concentration levels of the various dissolved gas components 504 at times other than the sampling dates during which the gas concentration levels were directly measured.

Example embodiments of the disclosure include or yield various technical features, technical effects, and/or improvements to technology. Example embodiments of the disclosure provide methods, systems, and computer-readable media for generating a predictive model using physically sampled data and sensor data captured by one or more sensors. The predictive model may be generated by solving an optimization problem that seeks to minimize a difference between the physically sampled data and a predicted change in a measurable parameter, where the predicted change is determined based at least in part on cumulative statistics determined from the sensor data. These aspects of the disclosure constitute technical features that yield the technical effect of being able to estimate the value of a measurable parameter (e.g., gas concentration levels in oil of an oil-immersed transformer) at any given point in time without having to directly measure the parameter. The value of the measurable parameter may be estimated at points in time between prior sampling events and/or at future points in time. As a result of these technical features and technical effects, example embodiments of the disclosure represent an improvement to existing fault detection techniques that rely solely on the direct measurement of measurable parameters. It should be appreciated that the above examples of technical features, technical effects, and improvements to other technological fields provided by example embodiments of the disclosure are merely illustrative and not exhaustive.

One or more illustrative embodiments of the disclosure have been described above. The above-described embodiments are merely illustrative of the scope of this disclosure and are not intended to be limiting in any way. Accordingly, variations, modifications, and equivalents of embodiments disclosed herein are also within the scope of this disclosure.

Illustrative Computer Architecture

Figure 4:
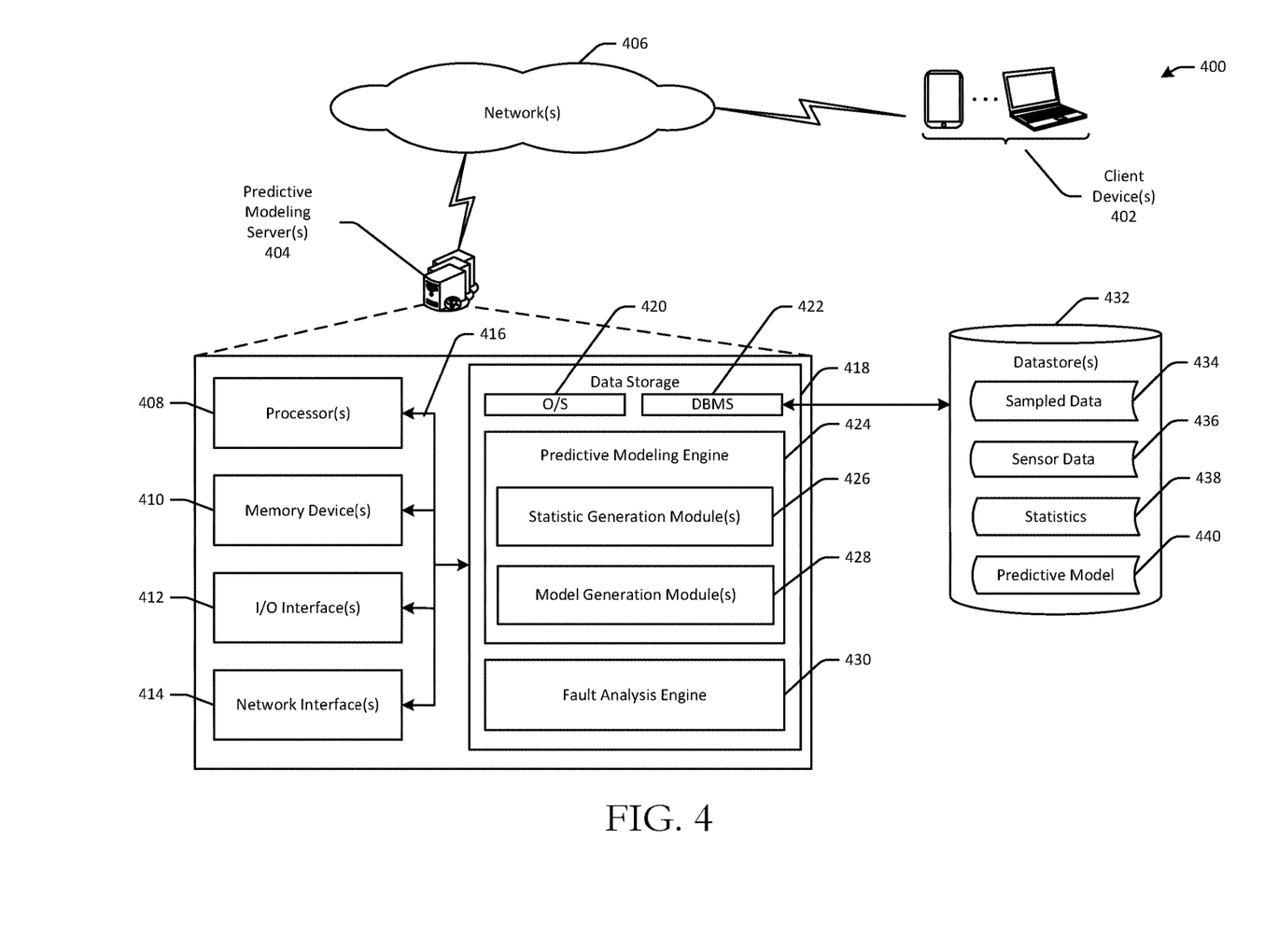
FIG. 4 is a schematic diagram of an illustrative computer architecture in accordance with one or more example embodiments of the disclosure.

FIG. 4 is a schematic diagram of an illustrative computer architecture 400 in accordance with one or more example embodiments of the disclosure. The architecture 400 may include one or more client devices 402 and one or more predictive modeling servers 404 configured to communicate over one or more networks 406. The client device(s) 402 may include one or more sensors configured to capture sensor data (e.g., SCADA data) relating to various operating parameters of equipment (e.g., an oil-immersed transformer). While the predictive modeling server 404 may be described herein in the singular, it should be appreciated that multiple instances of the predictive modeling server 404 may be provided, and functionality described in connection with the predictive modeling server 404 may be distributed across such multiple instances.

In an illustrative configuration, the predictive modeling server 404 may include one or more processors (processor(s)) 408, one or more memory devices 410 (generically referred to herein as memory 410), one or more input/output ("I/O") interface(s) 412, one or more network interfaces 414, and data storage 418. The predictive modeling server 404 may further include one or more buses 416 that functionally couple various components of the predictive modeling server 404.

The bus(es) 416 may include at least one of a system bus, a memory bus, an address bus, or a message bus, and may permit the exchange of information (e.g., data (including computer-executable code), signaling, etc.) between various components of the predictive modeling server 404. The bus(es) 416 may include, without limitation, a memory bus or a memory controller, a peripheral bus, an accelerated graphics port, and so forth. The bus(es) 416 may be associated with any suitable bus architecture including, without limitation, an Industry Standard Architecture (ISA), a Micro Channel Architecture (MCA), an Enhanced ISA (EISA), a Video Electronics Standards Association (VESA) architecture, an Accelerated Graphics Port (AGP) architecture, a Peripheral Component Interconnects (PCI) architecture, a PCI-Express architecture, a Personal Computer Memory Card International Association (PCMCIA) architecture, a Universal Serial Bus (USB) architecture, and so forth.

The memory 410 of the predictive modeling server 404 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In certain example embodiments, volatile memory may enable faster read/write access than non-volatile memory. However, in certain other example embodiments, certain types of non-volatile memory (e.g., FRAM) may enable faster read/write access than certain types of volatile memory.

In various implementations, the memory 410 may include multiple different types of memory such as various types of static random access memory (SRAM), various types of dynamic random access memory (DRAM), various types of unalterable ROM, and/or writeable variants of ROM such as electrically erasable programmable read-only memory (EEPROM), flash memory, and so forth. The memory 410 may include main memory as well as various forms of cache memory such as instruction cache(s), data cache(s), translation lookaside buffer(s) (TLBs), and so forth. Further, cache memory such as a data cache may be a multi-level cache organized as a hierarchy of one or more cache levels (L1, L2, etc.).

The data storage 418 may include removable storage and/or non-removable storage including, but not limited to, magnetic storage, optical disk storage, and/or tape storage. The data storage 418 may provide non-volatile storage of computer-executable instructions and other data. The memory 410 and the data storage 418, removable and/or non-removable, are examples of computer-readable storage media (CRSM) as that term is used herein.

The data storage 418 may store computer-executable code, instructions, or the like that may be loadable into the memory 410 and executable by the processor(s) 408 to cause the processor(s) 408 to perform or initiate various operations. The data storage 418 may additionally store data that may be copied to memory 410 for use by the processor(s) 408 during the execution of the computer-executable instructions. Moreover, output data generated as a result of execution of the computer-executable instructions by the processor(s) 408 may be stored initially in memory 410, and may ultimately be copied to data storage 418 for non-volatile storage.

More specifically, the data storage 418 may store one or more operating systems (O/S) 420; one or more database management systems (DBMS) 422 configured to access the memory 410 and/or one or more datastores 432; and one or more program modules, applications, engines, computer-executable code, scripts, or the like such as, for example, a predictive modeling engine 424 and a fault analysis engine 430. One or more engines of the predictive modeling server 404 may include one or more program modules configured to be executed to perform more specialized tasks. For example, the predictive modeling engine 424 may include one or more statistic generation modules 426 and one or more model generation modules 428. Any of the components depicted as being stored in data storage 418 may include any combination of software, firmware, and/or hardware. The software and/or firmware may include computer-executable code, instructions, or the like that may be loaded into the memory 410 for execution by one or more of the processor(s) 408 to perform any of the operations described earlier in connection with correspondingly named engines or modules.

Although not depicted in FIG. 4, the data storage 418 may further store various types of data utilized by components of the predictive modeling server 404 (e.g., any of the data depicted as being stored in the datastore(s) 432). Any data stored in the data storage 418 may be loaded into the memory 410 for use by the processor(s) 408 in executing computer-executable code. In addition, any data stored in the data storage 418 may potentially be stored in the datastore(s) 432 and may be accessed via the DBMS 422 and loaded in the memory 410 for use by the processor(s) 408 in executing computer-executable instructions, code, or the like.

The processor(s) 408 may be configured to access the memory 410 and execute computer-executable instructions loaded therein. For example, the processor(s) 408 may be configured to execute computer-executable instructions of the various program modules, applications, engines, or the like of the predictive modeling server 404 to cause or facilitate various operations to be performed in accordance with one or more embodiments of the disclosure. The processor(s) 408 may include any suitable processing unit capable of accepting data as input, processing the input data in accordance with stored computer-executable instructions, and generating output data. The processor(s) 408 may include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application Specific Integrated Circuit (ASIC), a Field-Programmable Gate Array (FPGA), a System-on-a-Chip (SoC), a digital signal processor (DSP), and so forth. Further, the processor(s) 408 may have any suitable microarchitecture design that includes any number of constituent components such as, for example, registers, multiplexers, arithmetic logic units, cache controllers for controlling read/write operations to cache memory, branch predictors, or the like. The microarchitecture design of the processor(s) 408 may be capable of supporting any of a variety of instruction sets.

Referring now to other illustrative components depicted as being stored in the data storage 418, the O/S 420 may be loaded from the data storage 418 into the memory 410 and may provide an interface between other application software executing on the predictive modeling server 404 and hardware resources of the predictive modeling server 404. More specifically, the O/S 420 may include a set of computer-executable instructions for managing hardware resources of the predictive modeling server 404 and for providing common services to other application programs (e.g., managing memory allocation among various application programs). In certain example embodiments, the O/S 420 may control execution of one or more of the program modules depicted as being stored in the data storage 418. The O/S 420 may include any operating system now known or which may be developed in the future including, but not limited to, any server operating system, any mainframe operating system, or any other proprietary or non-proprietary operating system.

The DBMS 422 may be loaded into the memory 410 and may support functionality for accessing, retrieving, storing, and/or manipulating data stored in the memory 410, data stored in the data storage 418, and/or data stored in the datastore(s) 432. The DBMS 422 may use any of a variety of database models (e.g., relational model, object model, etc.) and may support any of a variety of query languages. The DBMS 422 may access data represented in one or more data schemas and stored in any suitable data repository.

The datastore(s) 432 may include, but are not limited to, databases (e.g., relational, object-oriented, etc.), file systems, flat files, distributed datastores in which data is stored on more than one node of a computer network, peer-to-peer network datastores, or the like. The datastore(s) 432 may store various types of data including, without limitation, sampled data 434 (e.g., the physically sampled data 102); sensor data 436 (e.g., the sensor data 104); statistics 438 (e.g., any of the types of cumulative statistics described previously); and a predictive model 440 (e.g., the predictive model 112). It should be appreciated that in certain example embodiments, any of the datastore(s) 432 and/or any of the data depicted as residing thereon may additionally, or alternatively, be stored locally in the data storage 418.

Referring now to other illustrative components of the predictive modeling server 404, the input/output (I/O) interface(s) 412 may facilitate the receipt of input information by the predictive modeling server 404 from one or more I/O devices as well as the output of information from the predictive modeling server 404 to the one or more I/O devices. The I/O devices may include any of a variety of components such as a display or display screen having a touch surface or touchscreen; an audio output device for producing sound, such as a speaker; an audio capture device, such as a microphone; an image and/or video capture device, such as a camera; a haptic unit; and so forth. Any of these components may be integrated into the predictive modeling server 404 or may be separate. The I/O devices may further include, for example, any number of peripheral devices such as data storage devices, printing devices, and so forth.

The I/O interface(s) 412 may also include an interface for an external peripheral device connection such as universal serial bus (USB), FireWire, Thunderbolt, Ethernet port or other connection protocol that may connect to one or more networks. The I/O interface(s) 412 may also include a connection to one or more antennas to connect to one or more networks via a wireless local area network (WLAN) (such as Wi-Fi) radio, Bluetooth, and/or a wireless network radio, such as a radio capable of communication with a wireless communication network such as a Long Term Evolution (LTE) network, WiMAX network, 3G network, etc.

The predictive modeling server 404 may further include one or more network interfaces 414 via which the predictive modeling server 404 may communicate with any of a variety of other systems, platforms, networks, devices, and so forth. The network interface(s) 414 may enable communication, for example, with one or more other devices (e.g., a client device 402) via one or more of the network(s) 406 which may include, but are not limited to, any one or more different types of communications networks such as, for example, cable networks, public networks (e.g., the Internet), private networks (e.g., frame-relay networks), wireless networks, cellular networks, telephone networks (e.g., a public switched telephone network), or any other suitable private or public packet-switched or circuit-switched networks. The network(s) 406 may have any suitable communication range associated therewith and may include, for example, global networks (e.g., the Internet), metropolitan area networks (MANs), wide area networks (WANs), local area networks (LANs), or personal area networks (PANs). In addition, the network(s) 406 may include communication links and associated networking devices (e.g., link-layer switches, routers, etc.) for transmitting network traffic over any suitable type of medium including, but not limited to, coaxial cable, twisted-pair wire (e.g., twisted-pair copper wire), optical fiber, a hybrid fiber-coaxial (HFC) medium, a microwave medium, a radio frequency communication medium, a satellite communication medium, or any combination thereof.

It should be appreciated that the engines/modules depicted in FIG. 4 as being stored in the data storage 418 (or depicted in FIG. 1) are merely illustrative and not exhaustive and that processing described as being supported by any particular engine or module may alternatively be distributed across multiple engines, modules, or the like, or performed by a different engine, module, or the like. In addition, various program module(s), script(s), plug-in(s), Application Programming Interface(s) (API(s)), or any other suitable computer-executable code hosted locally on the predictive modeling server 404 and/or hosted on other computing device(s) accessible via one or more of networks, may be provided to support functionality provided by the engines/modules depicted in FIGS. 1 and 4 and/or additional or alternate functionality. Further, functionality may be modularized differently such that processing described as being supported collectively by the collection of engines/modules depicted in FIGS. 1 and 4 may be performed by a fewer or greater number of engines or program modules, or functionality described as being supported by any particular engine or module may be supported, at least in part, by another engine or program module. In addition, engines or program modules that support the functionality described herein may form part of one or more applications executable across any number of devices of the predictive modeling server 404 in accordance with any suitable computing model such as, for example, a client-server model, a peer-to-peer model, and so forth. In addition, any of the functionality described as being supported by any of the engines/modules depicted in FIGS. 1 and 4 may be implemented, at least partially, in hardware and/or firmware across any number of devices.

It should further be appreciated that the predictive modeling server 404 may include alternate and/or additional hardware, software, or firmware components beyond those described or depicted without departing from the scope of the disclosure. More particularly, it should be appreciated that software, firmware, or hardware components depicted as forming part of the predictive modeling server 404 are merely illustrative and that some components may not be present or additional components may be provided in various embodiments. While various illustrative engines/modules have been depicted and described as software engines or program modules stored in data storage 418, it should be appreciated that functionality described as being supported by the engines or modules may be enabled by any combination of hardware, software, and/or firmware. It should further be appreciated that each of the above-mentioned engines or modules may, in various embodiments, represent a logical partitioning of supported functionality. This logical partitioning is depicted for ease of explanation of the functionality and may not be representative of the structure of software, hardware, and/or firmware for implementing the functionality. Accordingly, it should be appreciated that functionality described as being provided by a particular engine or module may, in various embodiments, be provided at least in part by one or more other engines or modules. Further, one or more depicted engines or modules may not be present in certain embodiments, while in other embodiments, additional engines or modules not depicted may be present and may support at least a portion of the described functionality and/or additional functionality. Moreover, while certain engines modules may be depicted or described as sub-engines or sub-modules of another engine or module, in certain embodiments, such engines or modules may be provided as independent engines or modules or as sub-engines or sub-modules of other engines or modules.

One or more operations of the methods 200 or 300 may be performed by one or more predictive modeling servers 404 having the illustrative configuration depicted in FIG. 4, or more specifically, by one or more engines, program modules, applications, or the like executable on such predictive modeling server(s) 404. It should be appreciated, however, that such operations may be implemented in connection with numerous other system configurations.

The operations described and depicted in the illustrative methods of FIGS. 2 and 3 may be carried out or performed in any suitable order as desired in various example embodiments of the disclosure. Additionally, in certain example embodiments, at least a portion of the operations may be carried out in parallel. Furthermore, in certain example embodiments, less, more, or different operations than those depicted in FIGS. 2 and 3 may be performed.

Although specific embodiments of the disclosure have been described, one of ordinary skill in the art will recognize that numerous other modifications and alternative embodiments are within the scope of the disclosure. For example, any of the functionality and/or processing capabilities described with respect to a particular system, system component, device, or device component may be performed by any other system, device, or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for estimating a measurable parameter without having to obtain additional physically sampled data, the method comprising:

obtaining first data relating to the measurable parameter, the first data being obtained by directly measuring the measurable parameter in a physical sample associated with equipment, wherein the parameter is concentration of a dissolved gas component and the first data comprises a first concentration level of the dissolved gas component measured during a first time period and a second concentration level of the dissolved gas component measured during a second time period;

obtaining second data comprising sensor data captured by one or more sensors, the sensor data relating to one or more operating parameters of the equipment;

determining one or more cumulative statistics from the sensor data;

generating a predictive model using the one or more cumulative statistics and the first data, wherein generating the predictive model comprises:

determining an actual change in the concentration of the dissolved gas component between the first concentration level and the second concentration level;

determining a predicted change in the concentration of the dissolved gas component between the first time period and the second time period based at least in part on the sensor data, wherein determining the predicted change comprises determining an output of a function of the one or more cumulative statistics; and determining a solution to an optimization problem that minimizes a difference between the actual change in the concentration of the dissolved gas component and the predicted change in the concentration of the dissolved gas component; and estimating, using the predictive model, a value of the measurable parameter between the first time period and the second time period.

2. The method of claim 1, wherein the one or more cumulative statistics comprise at least one of a descriptive statistic, an accelerated decomposition condition statistic, or an accelerated decomposition event statistic.

3. The method of claim 1, wherein the physical sample is a sample of oil associated with an oil-immersed transformer.

4. The method of claim 1, wherein estimating a value of the measurable parameter using the predictive model comprises estimating a third concentration level of the dissolved gas component during a third time period between the first time period and the second time period, prior to the first time period, or after the second time period using the predictive model.

5. The method of claim 1, further comprising determining that a fault condition exists based at least in part on the value of the measurable parameter estimated using the predictive model.

6. The method of claim 1, wherein the equipment is a transformer, and wherein the one or more operating parameters comprise at least one of a voltage parameter, a current parameter, or a temperature parameter.

7. A system for estimating a measurable parameter without having to obtain additional physically sampled data, the system comprising:

at least one memory storing computer-executable instructions; and at least one processor configured to access the at least one memory and execute the computer-executable instructions to:

obtain first data relating to the measurable parameter, the first data being obtained by directly measuring the measurable parameter in a physical sample associated with equipment, wherein the parameter is concentration of a dissolved gas component and the first data comprises a first concentration level of the dissolved gas component measured during a first time period and a second concentration level of the dissolved gas component measured during a second time period;

obtain second data comprising sensor data captured by one or more sensors, the sensor data relating to one or more operating parameters of the equipment;

determine one or more cumulative statistics from the sensor data;

generate a predictive model using the one or more cumulative statistics and the first data, wherein the at least one processor is configured to generate the predictive model by executing the computer-executable instructions to:

determine an actual change in the concentration of the dissolved gas component between the first concentration level and the second concentration level;

determine a predicted change in the concentration of the dissolved gas component between the first time period and the second time period based at least in part on the sensor data, wherein the at least one processor is configured to determine the predicted change by executing the computer-executable instructions to determine an output of a function of the one or more cumulative statistics; and determine a solution to an optimization problem that minimizes a difference between the actual change in the concentration of the dissolved gas component and the predicted change in the concentration of the dissolved gas component; and estimate, using the predictive model, a value of the measurable parameter between the first time period and the second time period.

8. The system of claim 7, wherein the one or more cumulative statistics comprise at least one of a descriptive statistic, an accelerated decomposition condition statistic, or an accelerated decomposition event statistic.

9. The system of claim 7, wherein the physical sample is a sample of oil associated with an oil-immersed transformer.

10. The system of claim 7, wherein the at least one processor is configured to estimate a value of the measurable parameter using the predictive model by executing the computer-executable instructions to estimate a third concentration level of the dissolved gas component during a third time period between the first time period and the second time period, prior to the first time period, or after the second time period using the predictive model.

11. The system of claim 7, wherein the at least one processor is further configured to execute the computer-executable instructions to determine that a fault condition exists based at least in part on the value of the measurable parameter estimated using the predictive model.

12. The system of claim 7, wherein the equipment is a transformer, and wherein the one or more operating parameters comprise at least one of a voltage parameter, a current parameter, or a temperature parameter.

13. A computer program product for estimating a measurable parameter without having to obtain additional physically sampled data, the computer program product comprising a non-transitory storage medium readable by a processing circuit, the storage medium storing instructions executable by the processing circuit to cause a method to be performed, the method comprising:

obtaining first data relating to the measurable parameter, the first data being obtained by directly measuring the measurable parameter in a physical sample associated with equipment, wherein the parameter is concentration of a dissolved gas component and the first data comprises a first concentration level of the dissolved gas component measured during a first time period and a second concentration level of the dissolved gas component measured during a second time period;

obtaining second data comprising sensor data captured by one or more sensors, the sensor data relating to one or more operating parameters of the equipment;

determining one or more cumulative statistics from the sensor data;

generating a predictive model using the one or more cumulative statistics and the first data, wherein generating the predictive model comprises:

determining an actual change in the concentration of the dissolved gas component between the first concentration level and the second concentration level;

determining a predicted change in the concentration of the dissolved gas component between the first time period and the second time period based at least in part on the sensor data, wherein determining the predicted change comprises determining an output of a function of the one or more cumulative statistics; and     determining a solution to an optimization problem that minimizes a difference between the actual change in the concentration of the dissolved gas component and the predicted change in the concentration of the dissolved gas component; and estimating, using the predictive model, a value of the measurable parameter between the first time period and the second time period.

14. The computer program product of claim 13, wherein the one or more cumulative statistics comprise at least one of a descriptive statistic, an accelerated decomposition condition statistic, or an accelerated decomposition event statistic.

15. The computer program product of claim 13, wherein the physical sample is a sample of oil associated with an oil-immersed transformer.

16. The computer program product of claim 13, wherein estimating a value of the measurable parameter using the predictive model comprises estimating a third concentration level of the dissolved gas component during a third time period between the first time period and the second time period, prior to the first time period, or after the second time period using the predictive model.

17. The computer program product of claim 13, the method further comprising determining that a fault condition exists based at least in part on the value of the measurable parameter estimated using the predictive model.

* * * * *